United States Patent
Loxton et al.

(10) Patent No.: US 8,114,910 B2
(45) Date of Patent: Feb. 14, 2012

(54) ACIDIC COMPOSITION

(75) Inventors: Earle John Loxton, Somerset West (ZA); Rudolph Johannes Malan, Lynwood Glen (ZA); Stefan Coetzee, Somerset West (ZA)

(73) Assignee: Pfeinsmith S.A. (Pty) Ltd., Cape Town (ZA)

( * ) Notice: Subject to any disclaimer, the term of this patent is extended or adjusted under 35 U.S.C. 154(b) by 434 days.

(21) Appl. No.: 12/299,110

(22) PCT Filed: Apr. 26, 2007

(86) PCT No.: PCT/IB2007/051551
§ 371 (c)(1),
(2), (4) Date: Jan. 23, 2009

(87) PCT Pub. No.: WO2007/125492
PCT Pub. Date: Nov. 8, 2007

(65) Prior Publication Data
US 2009/0175957 A1    Jul. 9, 2009

(30) Foreign Application Priority Data
May 2, 2006 (ZA) .................... 2006/03457

(51) Int. Cl.
*A61K 9/14* (2006.01)
*A01N 43/04* (2006.01)
*A01N 37/00* (2006.01)
*A01N 37/10* (2006.01)
*A01N 37/44* (2006.01)
*A61K 31/70* (2006.01)
*A61K 31/19* (2006.01)

(52) U.S. Cl. .......... 514/569; 424/493; 514/23; 514/559; 514/566

(58) Field of Classification Search .............. None
See application file for complete search history.

(56) References Cited

U.S. PATENT DOCUMENTS

| | | | |
|---|---|---|---|
| 4,578,506 A | * | 3/1986 | Frank ............ 560/148 |
| 4,912,256 A | | 3/1990 | Cronje |
| 4,999,202 A | | 3/1991 | Cronje et al. |
| 5,204,368 A | | 4/1993 | Cronje et al. |
| 5,221,357 A | | 6/1993 | Brink |
| 5,599,977 A | | 2/1997 | Kiely et al. |

FOREIGN PATENT DOCUMENTS

| | | | |
|---|---|---|---|
| DE | 100 11 032 A1 | | 9/2001 |
| GB | 2 244 215 A | | 11/1991 |
| WO | WO-00/19999 A1 | | 4/2000 |
| WO | WO 2006000073 | * | 1/2006 |

OTHER PUBLICATIONS

Humic acid Wikipedia [online] retreived from: http://en.wikipedia.org/wiki/Humic_acid on Apr. 11, 11; 4 pages.*

* cited by examiner

*Primary Examiner* — Ernst Arnold
(74) *Attorney, Agent, or Firm* — Birch, Stewart, Kolasch & Birch, LLP

(57) ABSTRACT

A composition is provided which comprises an acidic component, generally fulvic acid, having a molecular weight not exceeding 20,000 Daltons and a low content of the elements aluminum, mercury, cadmium, chromium and lead. The acidic component is preferably carbohydrate derived and preferably using a wet oxidation process.

11 Claims, 1 Drawing Sheet

ACIDIC COMPOSITION

BACKGROUND OF THE INVENTION

This invention relates to acidic compositions.

Humic substances are present in nature and arise from the decay of plant and animal residues in the environment. These substances can be divided into humic acid and fulvic acid on the basis of their solubility in water as a function of pH. Fulvic acid is the fraction of humic substances that is soluble in water under all pH conditions and is in general lower in molecular size and weight and lower in colour intensity than humic acid.

Humic and fulvic acids can be derived from coals and other sources by wet or dry or other oxidation processes. A particularly suitable wet oxidation process for producing humic and fulvic acids from coal is that described in U.S. Pat. No. 4,912,256. Humic and fulvic acids derived from the wet oxidation of coal are often referred to as oxihumic and oxifulvic acids.

International Patent Publication WO 00/19999 discloses the use of oxifulvic acid in the treatment of inflammation, acne, eczema, and bacterial, fungal and viral infections.

U.S. Pat. Nos. 4,999,202 and 5,204,368 disclose compositions containing fulvic acid, salt or derivative thereof, which have bacteriostatic properties. The compositions are described as being useful as disinfectants.

SUMMARY OF THE INVENTION

According to the present invention, a composition is provided which comprises an acidic component, as an active ingredient, the acidic component having a molecular weight not exceeding 20 000 Daltons, and a low content of the elements aluminum, mercury, cadmium, chromium and lead.

The acidic component has a molecular weight not exceeding 20 000 Daltons, and preferably a molecular weight not exceeding 10000 Daltons, more preferably a molecular weight not exceeding 3000 Daltons.

Thus, the composition of the invention is substantially free of acidic components such as humic acid having a molecular weight exceeding 20,000 Daltons.

The acidic component in the composition of the invention may be in free acid form or in the form of a salt or other water soluble form.

The composition of the invention may contain water in which case the acidic component will be in solution in the water. The pH of the composition can vary over a wide range and be acidic, e.g. pH of 2.5 or lower, close to neutral or basic. The pH will be chosen to suit the requirements of the use to which the composition is put.

The composition may also be low in water content, e.g. having less than 10 weight percent water, or be substantially free of water.

An essential feature of the composition of the invention is that it has a low content of the elements aluminum, mercury, cadmium, chromium and lead. These elements are harmful to humans and should be avoided in pharmaceutical preparations. The total content of these elements preferably does not exceed 30 ppm (30 mg/l) and more preferably does not exceed 20 ppm. The composition of the invention has particular application as a pharmaceutical preparation or in the manufacture of a pharmaceutical preparation.

For many applications it is desirable for the composition to have a low content of silver, arsenic and beryllium. In one preferred form of the invention, the composition has a total content of these elements and the other elements set out above, below 30 ppm.

The composition of the invention may also have a low content of the elements cobalt, copper, iron, manganese, nickel, antimony, silicon, tin and zinc.

The acidic component of the composition of the invention is preferably derived from a carbohydrate. The carbohydrate is preferably a saccharide, i.e. a monosaccharide, disaccharide or polysaccharide, such as glucose, sucrose, or fructose. The carbohydrate can also be starch or cellulose.

The composition of the invention may be used in a wide variety of applications. For example it has application as an active pharmaceutical ingredient. It may be used in various medical therapeutic applications like the treatment of viral infections such as HIV, influenza, smallpox, SARS and herpes. The composition also has antibacterial properties, and is effective in treating a wide range of antibiotic resistant infections such as MRSA, *Klebsiella, Pseudomonas, Acinetobacter, Enterobacter* and *Proteus* sp. The composition possesses anti-fungal properties and is also effective in treating *Candida* infections. Fungal infections such as Tinia may also be treated with the composition of the invention.

The composition of the invention may be used as such as a pharmaceutical formulation or it may be used as a composition from which such a pharmaceutical formulation may be prepared. For example, the composition, when it contains water, may be used as such, suitably buffered, e.g. to a pH of 5 to 7, as a tonic or may be formulated into oral formulations such as capsules, liquid formulations such as syrups and the like or topical formulations such as creams. The composition substantially free of water, or containing a low water content, e.g. less than 10 percent, may be formulated into tablets or capsules.

The composition of the invention may contain other active ingredients, in addition to the acidic component.

The invention provides, according to another aspect, a method of producing a composition including the steps of providing a carbohydrate source, subjecting the source to wet oxidation to produce a reaction product comprising an acidic component in solution and treating the reaction product to remove substantially all of the acidic components having a molecular weight exceeding 20 000 Daltons. Removal of acidic components having a molecular weight exceeding 20 000 Daltons is preferably achieved by filtration in one or more filtration steps.

The wet oxidation preferably includes the steps of producing a solution or suspension of the carbohydrate in water, and subjecting the solution or suspension to oxidation under elevated temperature and pressure conditions producing the reaction product.

Oxidation will take place in the presence of an oxidizing agent such as oxygen or a peroxide and preferably oxygen.

The elevated temperature will typically be in the range 100 to 300 degrees centigrade and the pressure will be such that boiling of the water is prevented. Typically, the applied pressure will be in the range 1.5 to 5 MPa.

In one preferred form of the invention, the solution or suspension of the carbohydrate in water is passed continuously through a reactor where oxidation of the carbohydrate takes place. Typically, the solution or suspension is passed through the reactor at a rate of in the range 65 to 90 litres/hour.

It is preferred that water is removed from the reaction product, preferably after the removal of the acidic components of higher molecular weight, to produce a more concentrated reaction product or composition. Removal of water can be achieved by filtration or evaporation, for example.

The carbohydrate source is preferably a saccharide, i.e. polysaccharide, disaccharide or a monosaccharide, such as glucose, sucrose or fructose. The carbohydrate may also be starch or cellulose.

DESCRIPTION OF EMBODIMENTS OF THE INVENTION

Figure 1:
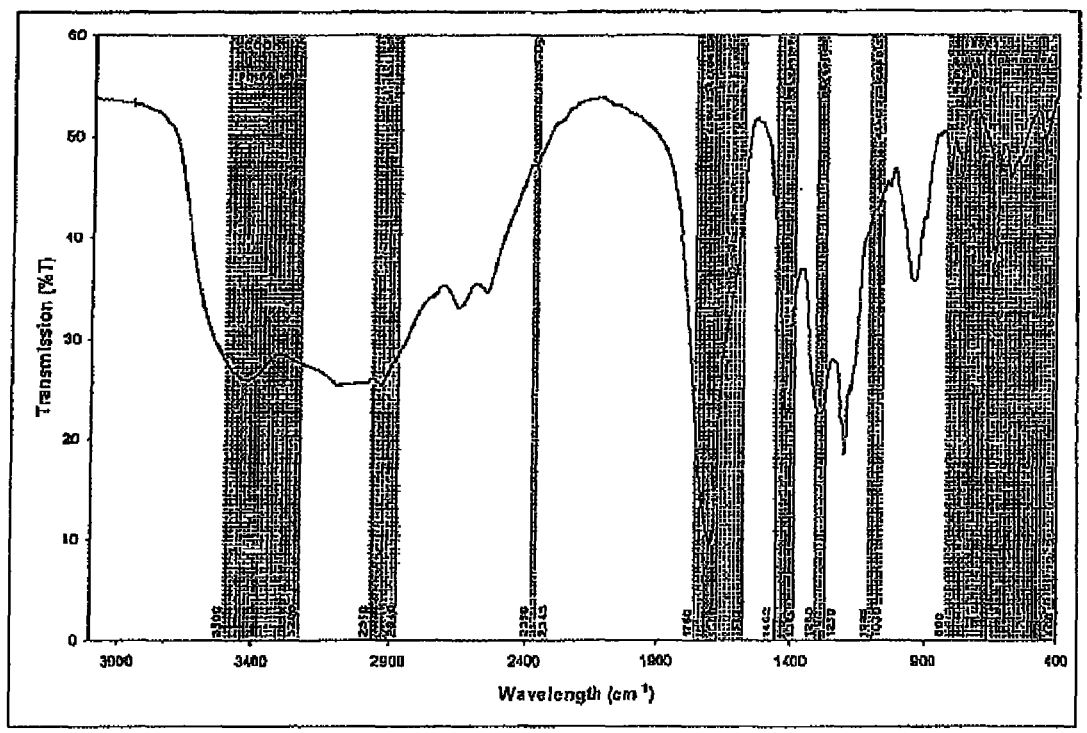
FIG. 1 illustrates a representative infrared spectrum of fulvic acid.

The acidic composition of the invention contains an acidic component, generally fulvic acid, having a molecular weight not exceeding 20,000 Daltons and a low metal content. The acidic component is preferably derived from a carbohydrate, particularly a saccharide. An example of producing such a composition will not be described.

Example 1

A fulvic acid containing composition was produced from a sugar source. The sugar can be a refined sugar or a raw sugar such as molasses. The sugar source was placed in a mixing tank and water added to produce a sugar solution having a specific gravity of 1.0 to 1.1. From the mixing tank the sugar solution was fed continuously at a rate in the range 65 to 90 litres/hour to a pressurized reaction vessel in the range 1.5 to 5 MPa (15 to 50 Bar) with a capacity of 150 to 250 litres where it was heated to a temperature in the range 100 to 300 degrees centigrade, preferably a starting temperature in the range 120 to 180 degrees centigrade. Oxygen was introduced into the reaction vessel, preferably through a series of diffusers to ensure an even distribution of oxygen through the reactor. The pressure of the oxygen was in the range 1.5 to 5.5 MPa (15 to 55 Bar) and the flow rate was in the range 10 to 20 kg/hour. Oxidation of the sugar occurred producing a solution containing fulvic and humic acids.

The solution from the oxidation was then subjected to various filtration stages. In the first stage, the solution was passed through a 0.2 micron filter element. The permeate was delivered to the next filtration stage. In this stage, the permeate was passed through a nanofiltration element. The permeate was then collected. This filtration step particularly removed acidic components, that had a molecular weight exceeding 800 Daltons. The permeate from the second filtration stage can optionally be passed to a third filtration stage where material, particularly acidic components, having a molecular weight lower than 200 Daltons is partially removed. In this stage, the solution is passed through a nanofiltration element. The concentrate is collected.

The composition or concentrate produced contained fulvic acid in solution having the following characteristics:

pH of between 1.4-2.1

SG of between 1 and 1.1

Metal Content: See Table 1 below

Molecular Weight of Acidic Component—46 to 800 Daltons

Three compositions produced as described in Example 1 were compared with a fulvic acid composition produced by the wet oxidation of bituminous coal according to the process described in U.S. Pat. No. 4,912,256. Two of the compositions, designated yellow and brown, were also filtered to remove acidic components below 200 Daltons and the third, designated black, was as described above. These three compositions were compared with the coal-derived fulvic acid using Fourier-transform infrared spectroscopy.

Infrared spectroscopy provides the most information about the functional groups present in fulvic acid compositions. FIG. 1 is a typical example of an infrared spectrum of a fulvic acid composition. The broad band between 3500 and 3200 $cm^{-1}$ is indicative of u(O—H) stretch of carboxylic, alcohol and phenol groups and the small peaks between 2950 and 2840 $cm^{-1}$ indicates symmetric and asymmetric u(C—H) stretch of aliphatic chains. Small bands visible between 2358 and 2343 $cm^{-1}$ are due to carbon dioxide ($CO_2$) and are therefore not significant in the interpretation of fulvic acid structure. Carbonyl groups of α, β unsaturated or aromatic esters as well as ketones are identified by the intense peak between 1760 and 1680 $cm^{-1}$. Some fractions have a peak between 1570 and 1685 $cm^{-1}$ that is probably due to u(C=O) stretch of carboxylic acids overlapping with u(C=C) of aromatic and conjugated double bonds. The peaks between 1462 and 1400 $cm^{-1}$ and at 1375 $cm^{-1}$ are due to δ ($CH_2$) and δ ($CH_3$) of alkyl chains respectively. Bands between 1280 and 1250 $cm^{-1}$ are due to u(C—O) of phenolic groups and bands between 1095 and 1030 $cm^{-1}$ indicate u(C—OH) and u(C—O—C) of ethers and alcohols. Terminal double bonds of alkanes or substituted phenolic compounds absorb between 800 and 400 $cm^{-1}$ but these absorption patterns are confounded by absorption of Si—C and covalent sulphur bonds.

Figure 2:
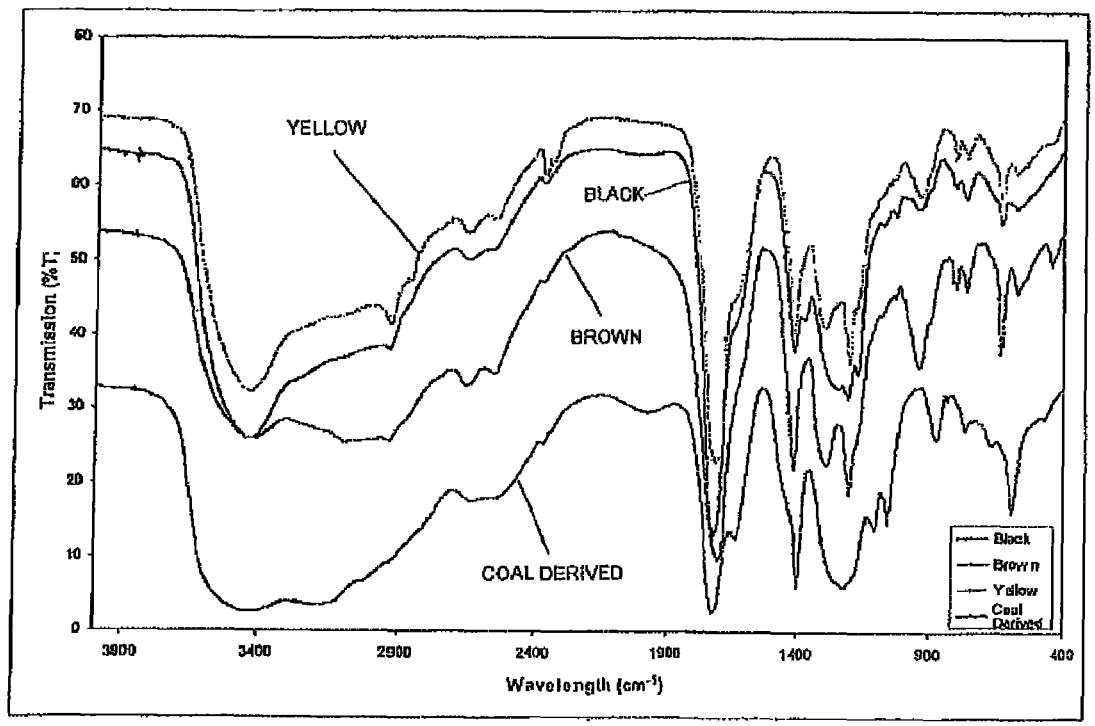
FIG. 2 illustrates the infrared spectra of the fulvic acid in three compositions of the invention and a coal-derived composition.

The three compositions of the invention (yellow, brown and black) were made by the method described in Example 1. Acidic components below 200 Daltons were removed for the yellow and brown compositions, but not for the black composition. The compositions were compared with one another. Aliphatic chains seem to be most prevalent in the brown composition and the shoulder peak between 1570 and 1680 $cm^{-1}$ is more prominent in the yellow and black compositions (FIG. 2). The yellow composition also shows a higher concentration of $CO_2$ than the other fractions. This is expected since the $CO_2$ would dissolve in the aqueous solution and permeate easily through all the filters used and concentrate in the permeate of the final filter, i.e. the yellow composition. Apart from these, there is little difference between the three compositions and the similarity in composition substantiates the common origin of the compositions. The coal-derived fulvic acid also shows a high absorption in the aliphatic region but this is more likely to be due to a slightly too concentrated sample being used. This is supported by the observation that most of the peaks of the coal derived fulvic acid are more rounded than the other fulvic acid compositions, a characteristic of higher sample concentrations in IR spectra.

From the above it will be noted that the acidic component in each of the yellow, brown, and black compositions is essentially the same as the acidic component in the coal-derived fulvic acid.

A significant difference, however, is in the metal content of the compositions of the invention compared with that of the coal-derived fulvic acid. The metal content of the brown composition was compared with that of coal-derived fulvic acid and water. The results are set out in Table 1 below:

TABLE 1

Heavy metal profile of Coal derived fulvic acid, carbohydrate derived fulvic acid (Brown) and the water used in the production of carbohydrate derived fulvic acid

| Metal | Coal Derived (ug/L) | Brown (Batch 96) (ug/L) | Water (ug/L) |
|---|---|---|---|
| Ag | 40 | 1 | 0 |
| Al | 913900 | 121 | 69 |
| As | 3630 | 11 | 4 |
| B | 433100 | 752 | 536 |
| Ba | 230 | 6 | 14 |
| Be | 8466 | 1 | 1 |
| Bi | 7 | 0 | 0 |
| Ca | 899 | 16 | 22 |
| Cd | 243 | 0 | 0 |
| Ce | 610 | 0 | 0 |
| Co | 29750 | 4 | 0 |
| Cr | 3288 | 36 | 2 |
| Cs | 165 | 1 | 1 |
| Cu | 4 | 1 | 0 |
| Dy | 668 | 0 | 0 |
| Er | 460 | 0 | 0 |
| Eu | 74 | 0 | 0 |
| Fe | 1182000 | 1880 | 38 |
| Ga | 1992 | 1 | 1 |
| Gd | 513 | 0 | 0 |
| Ge | 1468 | 0 | 0 |
| Hf | 267 | 0 | 0 |
| Hg | 4 | 0 | 0 |
| I | 38 | 29 | 3 |
| Ir | 1 | 0 | 0 |
| La | 214 | 0 | 0 |
| Li | 33390 | 6 | 4 |
| Lu | 70 | 0 | 0 |
| Mg | 2329 | 1 | 1 |
| Mn | 264700 | 81 | 2 |
| Mo | 161 | 11 | 0 |
| Nb | 576 | 0 | 0 |
| Nd | 740 | 0 | 0 |
| Ni | 24790 | 205 | 0 |
| Pb | 562 | 60 | 1 |
| Pd | 181 | 1 | 1 |
| Pr | 112 | 0 | 0 |
| Pt | 3 | 0 | 0 |
| Rb | 844 | 33 | 2 |
| Re | 2 | 0 | 0 |
| Rh | 1 | 0 | 0 |
| Ru | 0 | 0 | 0 |
| Sb | 42 | 1 | 0 |
| Se | 155 | 8 | 4 |
| Sm | 298 | 0 | 0 |
| Sn | 115 | 6 | 0 |
| Sr | 23140 | 27 | 54 |
| Ta | 2 | 1 | 0 |
| Te | 1 | 0 | 0 |
| Th | 365 | 0 | 0 |
| Ti | 22330 | 15 | 0 |
| Tl | 265 | 0 | 0 |
| Tm | 67 | 0 | 0 |
| U | 1131 | 1 | 0 |
| V | 45120 | 1 | 0 |
| W | 111 | 1 | 0 |
| Yb | 433 | 0 | 0 |
| Zn | 131 | 1 | 0 |
| Zr | 10730 | 5 | 1 |

It will be noted that the metal profile of the composition of the invention is significantly lower than that of the coal-derived fulvic acid with concentrations ranging from 5 to 50,000 times lower for the composition of the invention. This is particularly the case for harmful metals such as aluminum, mercury, cadmium, chromium and lead. For some metals such as bismuth, mercury, iridium, platinum the levels were too low to measure in the composition of the invention.

Fulvic acid compositions derived from plant and other organic natural sources also suffer from the disadvantage that they have high metal content as well as other contaminants such as pesticide residues. Further, the fulvic acid compositions from these sources have variable acid corn positions.

A composition of the invention was produced as described above and subjected to an antimicrobial efficacy test as follows:

Determination of the efficacy (quantitative comparison) of antimicrobials in solution using the radial diffusion inhibition method of fulvic acid.

Principle

In a standardized system (ignoring non antimicrobial components in the solution) the antimicrobial will diffuse into an agar medium. The distance diffused will be determined by the concentration of the antimicrobial substance. A standardized bacterial lawn is used as an indicator; no growth will occur where the antimicrobial concentration is high enough to kill the bacterial lawn, the greater the diameter of radial inhibition the stronger or more concentrated the antimicrobial component of the solution. Antimicrobials with different sized molecules cannot be directly compared with this method Equipment Colorimeter/Spectrophotometer with a 520 nm filter.
Bacterial Incubator; temperature kept at 37° C.
Punch; 0.45 mm aluminum tubing; Jennets Hobby Shop; Lynnwood Ridge Pretoria.
85 mm standard size petri dishes Definitions MC: MacConkey Agar with salt; Mast Laboratories; Importers Davies Diagnostics; tel. 011 7777600
Saline; 0.85% salt in distilled water. STERILE.
Sa: *Staphylococcus aureus* ATCC 12600

Essentialities

Depth of MC must be standardized to 4 mm in depth.
Sa lawn made up to an Abs OD of 0.07 in Saline Method Make up MC 1.2 gm+23 ml of distilled water; autoclave and cool to ±40° C.
Pour MC into a petri dish, leave to solidify
Punch out wells at least 23 mm apart. Radial zones of inhibition must not be distorted by an adjacent zone nor the edge of the petri dish.
Add 70 μL Sa suspension of an OD of 0.07 to the surface of the MC plate and spread evenly throughout it's surface. Precaution is taken not to allow wells to fill with the Sa suspension.
Add 50 μL of antimicrobial solution to the well.
Incubate for 24 Hr at 37° C.
Take two diameter readings at right angles to each other, of each zone of inhibition and calculate the average diameter.

It was found that the composition had an efficacy which has the following minimum limits:

Outer zone: Min 13.5 mm.
Inner zone: Min 8 mm

The composition described above may be used as an active pharmaceutical ingredient in the various therapeutic treatments described above. The composition, suitably buffered, may be used as such or may be formulated into various oral or topical formulations for such treatment.

In Example 1, the acidic composition resulting from the oxidation process was subjected to a number of filtration steps to remove components, particularly acidic components of molecular weight above 800 Daltons. It is possible to set the molecular weight threshold higher, for example remove components having a molecular weight above 3000 Daltons and leave components of lower molecular weight in the composition.

Water in the composition from the oxidation process may be removed by evaporation to concentrate the composition.

Compositions of the invention were also produced using carbohydrates other than sucrose. In particular, compositions were produced using glucose, fructose and maltodextrin as described in Examples 2 to 4.

Example 2

Glucose

A 10% by mass solution was made up by dissolving 1.5 kg of dry glucose in 13.5 liters of purified water. The resultant solution was equal to 15 kg. The solution was heated up in a batch reactor by means of an external heating coil driven by steam. The temperature of the solution was raised to 150 degrees Centigrade. At this point oxygen was added at a rate 1 kg/hr. For 3 minutes a sudden 5 degrees drop in temperature was observed after which the temperature gradually climbed to 160 degrees centigrade after 45 minutes. At this point the temperature climbed sharply to 240 degrees centigrade over the following 10 minutes. At this temperature the exothermic reaction continued for 5 minutes after which the temperature started dropping at which point the oxygen feed was shut off and the solution was allowed to cool down. Throughout the oxidation, a pressure was maintained to ensure the solution did not boil.

Example 3

Fructose

A 10% by mass solution was made up by dissolving 1.5 kg of dry crystallised fructose in 13.5 liters of purified water. The resultant solution was equal to 15 kg. The solution was heated up in a batch reactor by means of an external heating coil driven by steam. The temperature of the solution was raised to 150 degrees centigrade. At this point oxygen was added at a rate 1 kg/hr. For 24 minutes a gradual rise of 5 degrees centigrade in temperature was observed after which the temperature climbed steeply to 240 degrees centigrade over 20 minutes. At this temperature the exothermic reaction continued for 8 minutes after which the temperature started dropping at which point the oxygen feed was shut off and the solution was allowed to cool down. Throughout the oxidation, a pressure was maintained to ensure that the solution did not boil.

Example 4

Maltodextrin

A 10% by mass solution was made up by dissolving 1.5 kg of powdered maltodextrin in 13.5 liters of purified water. The resultant solution was equal to 15 kg. The solution was heated up in a batch reactor by means of an external heating coil driven by steam. The temperature of the solution was raised to 150 degrees centigrade. At this point oxygen was added at a rate 1 kg/hr. For 3 minutes a sudden 5 degrees drop in temperature was observed after which the temperature climbed gradually to 148 degrees centigrade after 50 minutes and stabilised. At this temperature the oxygen feed was shut off and the solution was allowed to cool down. Through the oxidation, a pressure was maintained to ensure that the solution did not boil.

The solutions in each of Examples 2 to 4, when subjected to the filtration steps of Example 1, result in solutions all containing fulvic acid and no acidic components above 20,000 Daltons being produced. Further, the solutions in each of Examples 2 to 4 all contained a low metal content similar to that set out in Table 1.

The invention claimed is:

1. A method of making a composition comprising fulvic acid as an active ingredient which includes the steps of providing a carbohydrate and subjecting the carbohydrate to wet oxidation to produce a reaction product comprising acidic components including fulvic acid in solution and treating the reaction product to remove substantially all of the acidic components having a molecular weight exceeding 20,000 Daltons;

wherein the wet oxidation includes the steps of producing a solution or suspension of the carbohydrate in water and subjecting the solution or suspension to elevated temperature and pressure conditions to oxidize the carbohydrate;

where elevated temperature is in the range 100 to 300 degrees centigrade and the pressure is such that boiling of the water is prevented; and wherein the carbohydrate is selected from the group consisting of a monosaccharide, a disaccharide, and a polysaccharide.

2. A method according to claim 1 wherein the pressure is from 1.5 to 5 MPa.

3. A method according to claim 1 wherein the solution or suspension is passed continuously through a reactor where the oxidation of the carbohydrate takes place.

4. A method according to claim 3 wherein the solution or suspension is passed through the reactor at a rate of in the range 65 to 90 liters/hour.

5. A method according to claim 1 wherein oxidation takes place in the presence of an oxidizing agent.

6. A method according to claim 5 wherein the oxidizing agent is oxygen.

7. A method according to claim 5 wherein the oxidizing agent is a peroxide.

8. A method according to claim 1 wherein the removal of acidic components is by filtration.

9. A method according to claim 1 wherein water is removed from the reaction product to concentrate the reaction product.

10. A method of claim 9 wherein the removal of the water is by filtration or evaporation.

11. The method of claim 1, wherein the fulvic acid composition contains a content of elements aluminum, mercury, cadmium, and lead not exceeding 30 ppm.

* * * * *